United States Patent
De Ridder

(10) Patent No.: US 7,315,761 B2
(45) Date of Patent: Jan. 1, 2008

(54) ELECTRICAL STIMULATION SYSTEM AND METHOD FOR TREATING TINNITUS

(75) Inventor: Dirk De Ridder, Zelzate (BE)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 10/993,888

(22) Filed: Nov. 19, 2004

(65) Prior Publication Data

US 2005/0159792 A1    Jul. 21, 2005

Related U.S. Application Data

(60) Provisional application No. 60/523,711, filed on Nov. 20, 2003.

(51) Int. Cl.
*A61N 1/05* (2006.01)
*H04R 5/00* (2006.01)
*A61F 11/04* (2006.01)

(52) U.S. Cl. ............................. 607/55; 607/56; 607/57; 607/45; 607/118; 600/25; 623/10

(58) Field of Classification Search ............ 607/55–57, 607/73, 45, 118; 600/25; 623/10
See application file for complete search history.

(56) References Cited

U.S. PATENT DOCUMENTS

| 4,541,432 | A | * | 9/1985 | Molina-Negro et al. ...... 607/46 |
| 5,496,369 | A | | 3/1996 | Howard, III |
| 5,697,975 | A | | 12/1997 | Howard, III et al. |
| 5,713,847 | A | | 2/1998 | Howard, III et al. |
| 5,735,885 | A | | 4/1998 | Howard, III et al. |
| 5,788,656 | A | | 8/1998 | Mino |
| 6,210,321 | B1 | | 4/2001 | Di Mino et al. |
| 6,295,472 | B1 | * | 9/2001 | Rubinstein et al. ........... 607/55 |
| 6,456,886 | B1 | | 9/2002 | Howard, III et al. |
| 6,529,774 | B1 | * | 3/2003 | Greene ....................... 600/545 |
| 6,597,954 | B1 | * | 7/2003 | Pless et al. ................... 607/62 |
| 6,656,172 | B1 | | 12/2003 | Hildebrand |

(Continued)

FOREIGN PATENT DOCUMENTS

WO    WO-01/08617 A1    2/2001

OTHER PUBLICATIONS

Reorganization of the auditory cortex, Muhlnickel et al., PNAS, vol. 95, Issue 17, 103040-10343, Aug. 1998.*

(Continued)

*Primary Examiner*—Carl Layno
*Assistant Examiner*—Natasha Patel
(74) *Attorney, Agent, or Firm*—Christopher S. L. Crawford; Peter Lando; Melissa Acosta

(57) ABSTRACT

According to one aspect, an electrical stimulation system for treating tinnitus is provided. The system includes an electrical stimulation lead adapted for implantation into the person's skull for electrical stimulation of target brain tissue located in the person's temporal lobe. The lead includes one or more electrodes adapted to be positioned near the target brain tissue and to deliver electrical stimulation energy to the target brain tissue. The system also includes a stimulation source operable to generate signals for transmission to the electrodes of the lead to cause the electrodes to deliver electrical stimulation energy to the target brain tissue located in the person's temporal lobe to reduce tinnitus effects.

23 Claims, 5 Drawing Sheets

U.S. PATENT DOCUMENTS

| | | | |
|---|---|---|---|
| 2002/0091419 A1* | 7/2002 | Firlik et al. | 607/45 |
| 2003/0135248 A1* | 7/2003 | Stypulkowski | 607/73 |
| 2005/0043646 A1 | 2/2005 | Viirre et al. | |
| 2005/0070971 A1* | 3/2005 | Fowler et al. | 607/45 |

OTHER PUBLICATIONS

McIntyre, Cameron C., et al.; Extracellular Stimulation of Central Neurons: Influence of Stimulus Waveform and Frequency on Neuronal Output; J. Neurophysiol., 88:1592-1604, 2002.

Leinonen, L., et al.; Functional Properties of Neurons in the Temporo-parietal Association Cortex of Awake Monkey; Exp. Brain Res., 39:203-215, 1980.

Fu, Kai-Ming G., et al.; Auditory Cortical Neurons Respond to Somatosensory Stimulation; The Journal of Neuroscience, 23(20):7510-7515, 2003/.

De Ridder, Dirk, et al.; Magnetic and electrical stimulation of the auditory cortex for intractable tinnitus: J. Neurosurg, 100:560-564, 2004.

Moller, Aage R., et al.; Some Forms of Tinnitus May Involve the Extralemniscal Auditory Pathway; Laryngoscope, 102:1165-1171, 1992.

De Ridder, Dirk, et al.; Comments to Tinnitus and Auditory Cortex—Letter to the Editor by Matthew A. Howard III, M.D.; J. Neurosurg., 101:171-172, 2004.

Chiry, Oriana, et al.; Patterns of calcium-binding proteins support parallel and hierarchical organization of human auditory areas; European Journal of Neuroscience, 17:397-40, 2003.

Foxe, John J., et al.; Research Report—Multisensory auditory-somatosensory interactions in early cortical processing revealed by high-density electrical mapping; Cognitive Brain Research, 10:77-83, 2000.

Foxe, John J., et al.; Auditory-Somatosensory Multisensory Processing in Auditory Association Cortex: An fMRI Study; J. Neurophysiol., 88:540-543, 2002.

Eichhammer, Peter, et al.; Brief Report: Neuronavigated Repetitive Transcranial Magnetic Stimulatin in Patients with Tinnitus: A short Case Series; Biol. Psychiatry, 54:862-865, 2003.

Jones, Edward G.; The thalamic matrix and thalamocortical synchrony; Trends in Neurosciences, 24(10):595-601, 2001.

He, Jufang, et al.; Differential Distribution of Burst and Single-Spike Responses in Auditory Thalamus; J. Neurophysiol., 88:2152-2156, 2002.

Lenz, F. A., et al.; Neuronal Activity in the region of the Thalamic Principal Sensory Nucleus (*Ventralis caudalis*) in Patients with Pain Following Amputations; Neuroscience, 86(4):1065-1081, 1998.

Lisman, John E.; Bursts as a unit of neural information: making unreliable synapses reliable; Trends Neurosci., 20(1):38-43, 1997.

Mirz, Frank, et al.; Positron emission tomography of cortical centers of tinnitus; Hearing Research, 134:133-144, 1999.

Tardiff, E., et al.; Patterns of Calcium-Binding Proteins in Human Inferior Colliculus; Identification of Subdivisions and Evidence for Putative Parallel Systems; Neuroscience, 116:1111-1121, 2003.

Laszig, Roland, et al.; Benefits of Bilateral Electrical Stimulation with the Nucleus Cochlear Implant in Adults: 6-Month Postoperative Results; Otology & Neurotology, 25:958-968, 2004.

Huang, Ying-Zu, et al.; Report—Theta Burst Stimulation of the Human Motor Cortex; Neuron, 45:201-206, 2005.

Langguth, Berthold, et al.; NeuroReport—Neuronavigated rTMS in a patient with chronic tinnitus. Effects of 4 weeks treatment; Auditory and Vestibular Systems, 14(7):977-980, 2003.

Zhang, J.S., et al.; Fos-like immunoreactivity in auditory and nonauditory brain structures of hamsters previously exposed to intense sound; Exp Brain Res, 153:655-660, 2003.

Wallhausser-Franke, E., et al.; Expression of c-fos in auditory and non-auditory brain regions of the gerbil after manipulations that induce tinnitus; Exp Brain Res, 153:649-654, 2003.

Shulman, Abraham; A Final Common Pathway for Tinnitus—The Medial Temporal Lobe System; International Tinnitus Journal, 1:115-126, 1995.

* cited by examiner

ELECTRICAL STIMULATION SYSTEM AND METHOD FOR TREATING TINNITUS

RELATED APPLICATIONS

This application claims the benefit under 35 U.S.C. § 119(e) of U.S. Provisional Application Ser. No. 60/523,711, filed Nov. 20, 2003, and International Application No. PCT/US04/038525 filed Nov. 17, 2004.

TECHNICAL FIELD OF THE INVENTION

This invention relates generally to electrical stimulation of a person's brain and in particular to an electrical stimulation system and method for treating tinnitus.

BACKGROUND

Tinnitus is a distressing symptom afflicting 10 to 15 percent of the general population. Twenty percent of those afflicted suffer from a significantly decreased quality of life; for example, many experience insomnia, depression, and other affective disorders.

When sound waves hit the eardrum, they are transmitted via the middle ear bones to the cochlea. In the cochlea, the sound waves are translated into neural patterns which are transferred via the cochlear nerve to the brainstem and then to the auditory cortex of the brain. The auditory system is organized in such a way that in the cochlea specific hair cells are activated by specific frequencies. This tonotopic organization is found throughout the auditory system. In particular, the auditory cortex is organized such that specific areas process the auditory information of specific frequencies.

Any lesion of the auditory tract that influences the normal function of the tract can generate tinnitus. In Meniere's disease, tinnitus is caused by a dysfunction of the cochlea; in acoustic neuroma, tinnitus is caused by a lesion of the vestibular nerve compressing the cochlear nerve; and in temporal brain tumor located in or near the auditory cortex, tinnitus is caused by direct interference with auditory cortex processing. The way in which tinnitus arises remains a matter of debate. However, some recent authors have suggested that tinnitus can be considered as an auditory phantom phenomenon similar to the phantom pain that arises after amputations.

Nerves and the brain are not hardwired, but are rather a constantly adapting network based on Darwinist principals. Nerve tracts are made up of nerve cells, each having a very specific function. Nerve cells that survive are those that are best suited for a specific function, which explains why humans have many more brain cells at birth than at the age of three years. Any change in a human's environment causes the brain to adapt to better process the changing incoming information. At birth, the auditory system is not completely hardwired and becomes functional only after it is exposed to environmental sounds. This exposition to sounds leads to a tonotopy that results from the death of synapses and brain cells that are not fit for a specific function, much as a sculpture is formed by removing the unnecessary marble from an original marble block. In the resulting tonotopy formed by exposure to sounds during the neonatal period, every brain cell processes a specific sound frequency only connected with those hair cells of the cochlea that process the same sound frequency.

When a lesion of the auditory tract occurs—for example, a lesion of the high frequencies caused by a sound trauma or the use of particular antibiotics—brain cells that process particular frequencies may become inactive. In order to prevent their death due to inactivity, the inactive cells grow into neighboring areas of the auditory cortex and thus begin to process other frequencies. For example, if a lesion of the high frequencies occurs, the brain cells may adapt to process middle frequencies in order to remain active. This process of cells altering their functions in accordance with changing demands is known as neural plasticity, or neuroplasticity. The mismatch between the genetically determined function of such cells and their active adapted processing leads to the conscious phenomenon referred to as tinnitus. This cortical reorganization can be demonstrated by a functional MRI (fMRI), PETscan, or magneto-encephalographic study.

It has been demonstrated that electrical stimulation of the auditory cortex in humans can reorganize the tonotopy of the cortex. External techniques have been used to electrically stimulate the auditory cortex in order to reorganize the tonotopy of the cortex to suppress the effects of tinnitus. For example, transcranial magnetic stimulation (TMS) devices have been used external to a person's head to stimulate the person's auditory cortex in order to provide temporary relief from the effects of tinnitus.

SUMMARY OF THE INVENTION

The electrical stimulation system and method of the present invention may reduce or eliminate certain problems and disadvantages associated with previous techniques for treating tinnitus.

According to one aspect, an electrical stimulation system for treating tinnitus is provided. The system includes an electrical stimulation lead adapted for implantation into the person's skull for electrical stimulation of target brain tissue located in the person's temporal lobe. The lead includes one or more electrodes adapted to be positioned near the target brain tissue and to deliver electrical stimulation energy to the target brain tissue. The system also includes a stimulation source operable to generate signals for transmission to the electrodes of the lead to cause the electrodes to deliver electrical stimulation energy to the target brain tissue located in the person's temporal lobe to reduce tinnitus effects.

Particular embodiments of the present invention may provide one or more technical advantages. According to the present invention, an electrical stimulation system is used to provide electrical stimulation of the brain to treat tinnitus. In particular, an electrical stimulation lead having a number of electrodes is implanted inside a person's skull such that one or more of the electrodes are located adjacent target brain tissue within the area of cortical reorganization in the temporal lobe of the person's brain. The electrodes deliver electrical stimulation energy to the target brain tissue, which partially or completely suppresses or otherwise reduces the person's tinnitus, which may significantly increase the person's quality of life. The electrical stimulation lead may be precisely positioned using a neuronavigation system that includes brain imaging and mapping data received from an FMRI of the person's brain. In addition, non-invasive transcranial magnetic stimulation (TMS) of the target brain tissue may be performed before surgically implanting the electrical stimulation lead in order to determine whether the person is a candidate for receiving an implanted electrical stimulation system.

In certain embodiments, the electrical stimulation system may also be able to provide electrical stimulation of the brain to prevent, delay, or otherwise reduce neuroplasticity effects that may be associated with the tinnitus suppressing electrical stimulation of the brain. As a result, in certain embodiments, the efficacy period associated with a particular set of stimulation parameters may be extended. This may help prevent the additional time and expense associated with one or more return visits to the treating physician for determining and entering new sets of efficacious parameters. Especially where the treatment is to continue over a relatively long period of time, such as a number of months or years, avoiding this additional time and expense may provide a significant advantage. As another example, in other situations, the further development of neuroplasticity effects already in existence due to injury or disease may be prevented, delayed, or otherwise reduced, or such pre-existing neuroplasticity effects may be reversed in whole or in part. As a result, in certain embodiments, tinnitus resulting from such pre-existing neuroplasticity effects may be prevented from progressing further, may be reduced, or may even be eliminated.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which.

DESCRIPTION OF EXAMPLE EMBODIMENTS

According to the present invention, an electrical stimulation system is used to provide electrical stimulation of the brain to treat tinnitus. In particular, an electrical stimulation lead having a number of electrodes is implanted inside a person's skull such that one or more of the electrodes are located adjacent target brain tissue near the location of the damage or the origin of the abnormal brain activity, more specifically within the temporal lobe of the person's brain. The electrodes deliver electrical stimulation energy to the target brain tissue, which partially or completely suppresses or otherwise reduces the person's tinnitus, which may significantly increase the person's quality of life. The electrical stimulation lead may be precisely positioned using a neuronavigation system that includes brain imaging and mapping data received from an FMRI of the person's brain. Non-invasive transcranial magnetic stimulation (TMS) of the target brain tissue may be performed before surgically implanting the electrical stimulation lead in order to determine whether the person is a candidate for receiving an implanted electrical stimulation system.

Figure 1A:
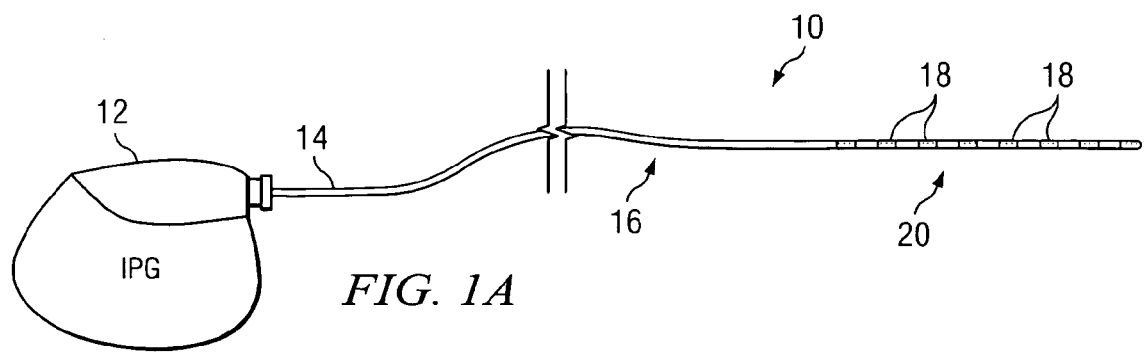
FIGS. 1A-1B illustrate example electrical stimulation systems for treating tinnitus and, in certain embodiments, providing reduced neuroplasticity effects in a person's brain.
Figure 1B:
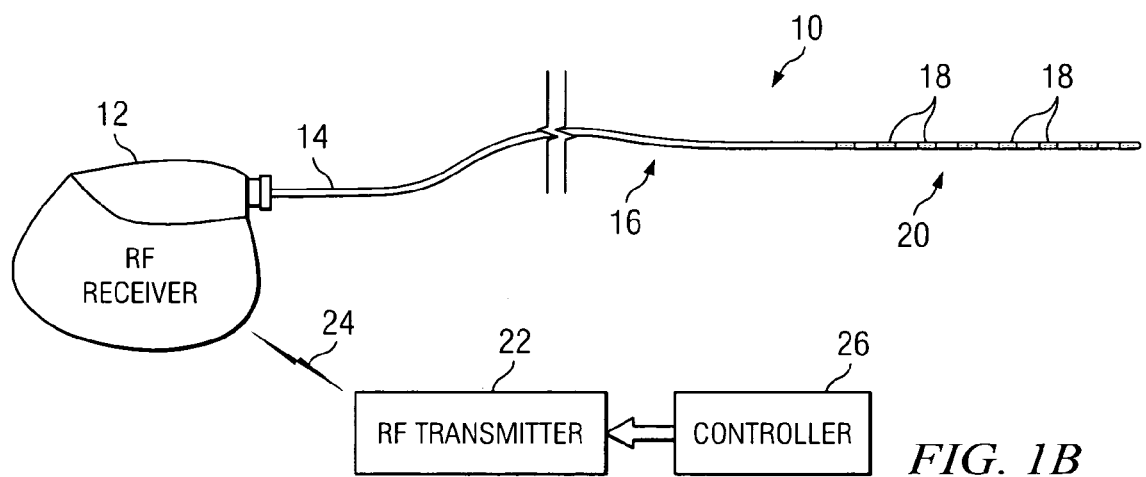

FIGS. 1A-1B illustrate example electrical stimulation systems 10 for treating tinnitus and, in certain embodiments, providing reduced neuroplasticity effects in a person's brain. Stimulation system 10 generates and applies a stimulus to a target area of the brain located in the temporal lobe to reduce tinnitus effects in a person's brain. In general terms, stimulation system 10 includes an implantable electrical stimulation source 12 and an implantable electrical stimulation lead 14 for applying the stimulation signal to the target brain tissue. In operation, both of these primary components are implanted in the person's body, as discussed below with reference to FIG. 3. Stimulation source 12 is coupled to a connecting portion 16 of electrical stimulation lead 14. Stimulation source 12 controls the electrical signals transmitted to one or more electrodes 18 located on a stimulating portion 20 of electrical stimulation lead 14, located adjacent the target brain tissue, according to suitable signal parameters (e.g., duration, intensity, frequency, etc.). A doctor, the patient, or another user of stimulation source 12 may directly or indirectly input signal parameters for controlling the nature of the electrical stimulation provided.

In one embodiment, as shown in FIG. 1A, stimulation source 12 includes an implantable pulse generator (IPG). An example IPG may be one manufactured by Advanced Neuromodulation Systems, Inc., such as the Genesis® System, part numbers 3604, 3608, 3609, and 3644. In another embodiment, as shown in FIG. 1B, stimulation source 12 includes an implantable wireless receiver. An example wireless receiver may be one manufactured by Advanced Neuromodulation Systems, Inc., such as the Renew® System, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. An example wireless transmitter 122 may be one manufactured by Advanced Neuromodulation Systems, Inc., such as the Renew® System, part numbers 3508 and 3516.

FIGS. 2A-2I illustrate example electrical stimulation leads 14 that may be used for treating tinnitus and, in certain embodiments, providing reduced neuroplasticity effects in a person's brain. As described above, each of the one or more leads 14 incorporated in stimulation system 10 includes one or more electrodes 18 adapted to be positioned near the target brain tissue and used to deliver electrical stimulation energy to the target brain tissue in response to electrical signals received from stimulation source 12. A percutaneous lead 14, such as example leads 14a-d, includes one or more circumferential electrodes 18 spaced apart from one another along the length of lead 14. Circumferential electrodes 18 emit electrical stimulation energy generally radially in all directions. A laminotomy or paddle style lead 14, such as example leads 14*e-i*, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, the present invention contemplates stimulation system 10 including any suitable type of lead 14 in any suitable number. In addition, the leads may be used alone or in combination. For example, unilateral stimulation of the brain is typically accomplished using a single lead 14 implanted in one side of the brain, while bilateral stimulation of the brain is typically accomplished using two leads 14 implanted in opposite sides of the brain.

Figure 3:
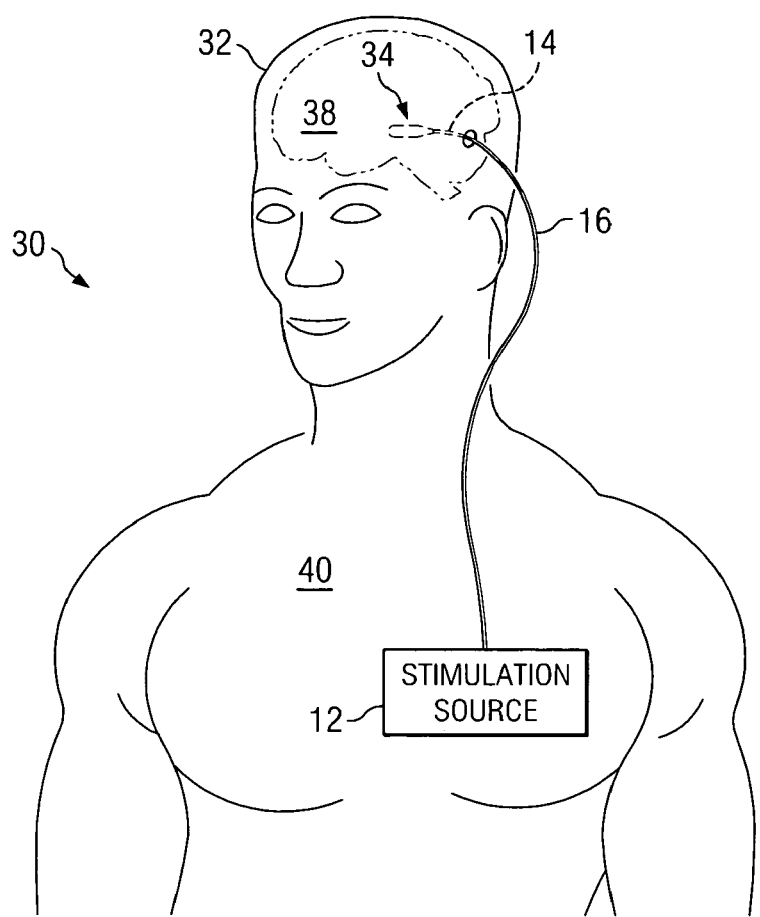
FIG. 3 illustrates example placement of the electrical stimulation system shown in FIGS. 1A-1B within a person's body.

FIG. 3 illustrates example placement of the electrical stimulation system 10 shown in FIGS. 1A-1B within a person's body 30. Electrical stimulation lead 14 is implanted under the person's skull 32 adjacent the temporal lobe 34 of the person's brain. In certain embodiments, electrical stimulation lead 14 is positioned within the extradural region adjacent the brain such that one or more electrodes 18 are located adjacent the area of cortical reorganization 38 within the temporal lobe 34. In other embodiments, electrical stimulation lead 14 is located at least partially within or below the dura mater adjacent the area of cortical reorganization 38. Geographically, electrical stimulation lead 14 may be inserted into the cortex or deeper layers of the brain.

Typical neurogeographical locations for lead placement in the auditory cortex include the primary auditory cortex, AI, also known as the transverse temporal gyri of Heschl (Brodman's areas 41 and 42), the secondary auditory cortex, AII (Brodman's areas 22 and 52), and the remote projection region. Authorities may vary in assigning Brodman's area 42 to the primary or secondary auditory cortex, but Brodman's area 42 is a placement location for one embodiment. Other embodiments may place electrical stimulation lead 14 at the ventral medial geniculate, which projects almost entirely to AI. Other embodiments may place electrical stimulation lead 14 in the surrounding auditory areas, which receive projections from the rest of the geniculate body. Still other embodiments may place electrical stimulation lead 14 in the medial geniculate body, which is the major auditory nucleus of the thalamus.

Stimulation source 12 is implanted within a subcutaneous pocket within the person's torso 40 (such as in or near the chest area or buttocks), and connecting portion 16 is tunneled, at least in part, subcutaneously underneath the person's skin to connect stimulation source 12 with the electrical stimulation lead 14. However, stimulation source 12 may be located at any suitable location within the person's body 30 according to particular needs.

Figure 4:
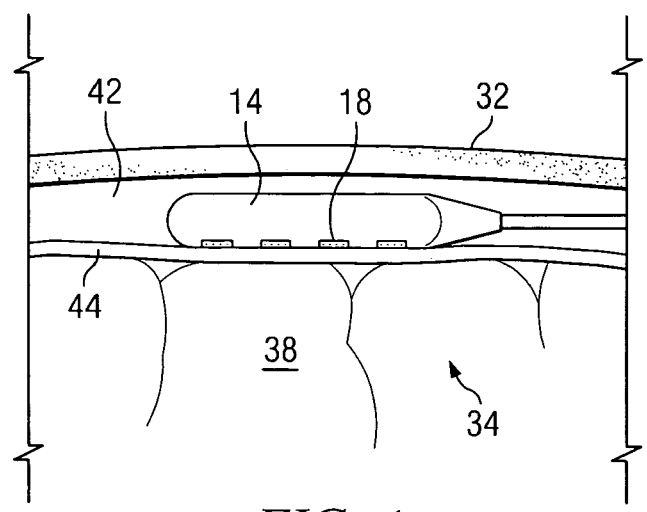
FIG. 4 is a cross-section of a portion of the person's head shown in FIG. 3, illustrating an example location of the electrical stimulation lead.

FIG. 4 is a cross-section of a portion of the person's head shown in FIG. 3, illustrating an example location of electrical stimulation lead 14. In certain embodiments, as discussed above, electrical stimulation lead 14 is located in the extradural region 42 outside the dura mater 44 and adjacent the area of cortical reorganization 38 within the temporal lobe 34 of the brain.

Figure 5:
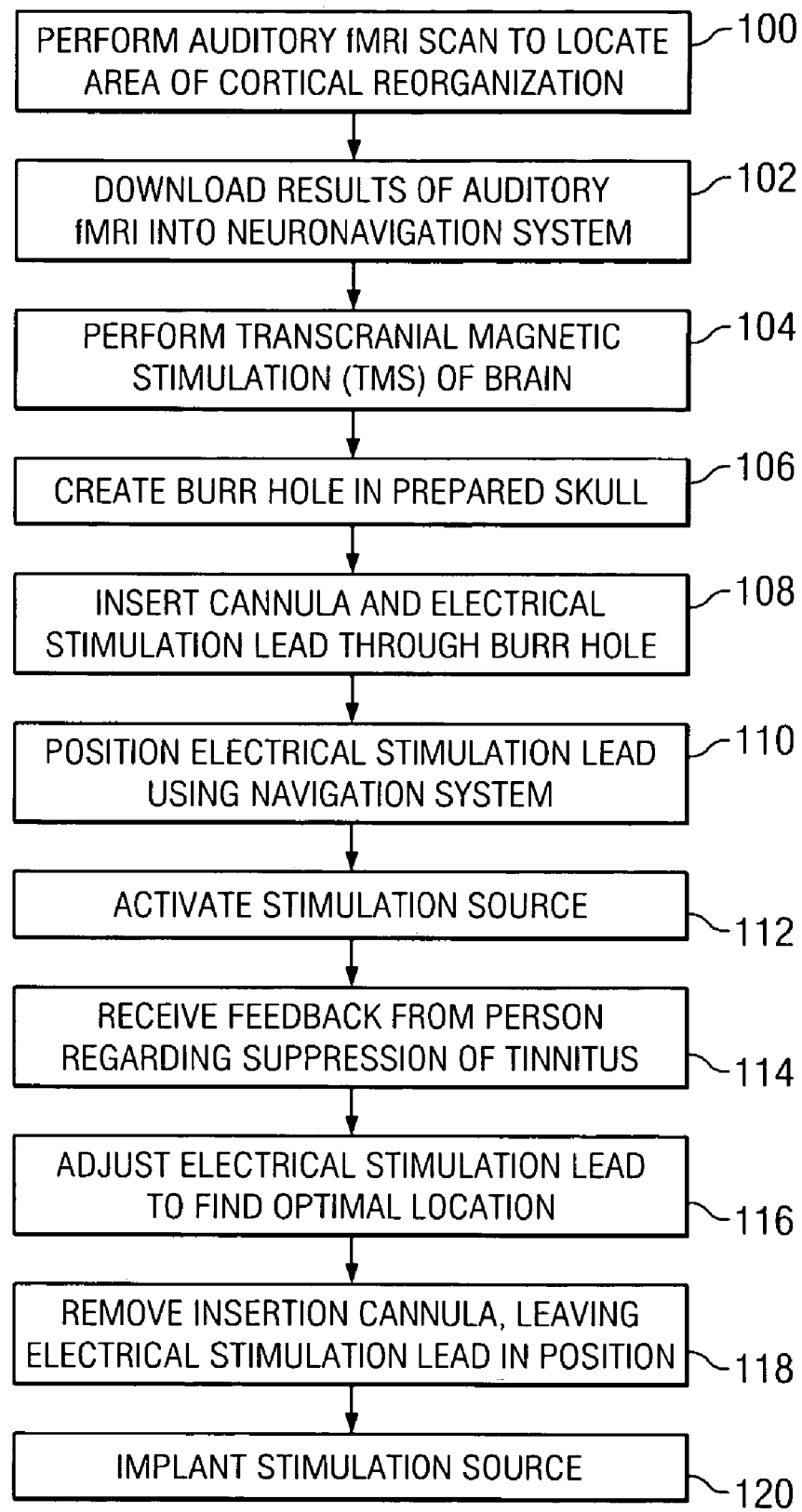
FIG. 5 illustrates an example method for determining the target location and implanting the stimulation system of FIGS. 1A-1B into a person in order to stimulate the temporal lobe to treat tinnitus.

FIG. 5 illustrates an example method for determining the target location and implanting the stimulation system 10 of FIGS. 1A-1B into a person in order to stimulate the temporal lobe 34 of the person's brain to treat tinnitus. At step 100, an auditory fMRI scan of the person's brain may be performed in order to locate the area of cortical reorganization 38 in the temporal lobe 34. The auditory fMRI scan combines a normal brain scan and a scan performed during auditory exposure. At step 102, the results of the fMRI are downloaded into a neuronavigation system. At step 104, TMS of the area of cortical reorganization 38 may be performed to determine whether the person is a candidate for receiving an implanted electrical stimulation system 10. The TMS process, which is a non-invasive technique of activating or deactivating focal areas of the brain, is guided by the navigation system that includes the fMRI data obtained at step 100. If the TMS process is successful in suppressing or otherwise reducing the area of cortical reorganization 38, thereby suppressing the person's tinnitus, the person may be considered for receiving an implanted electrical stimulation system 10.

Electrical stimulation system 10 is implanted inside the person at steps 106 through 118. At step 106, the skull 32 is first prepared by exposing the skull 32 and creating a burr hole in the skull 32. A burr hole cover may be seated within the burr hole and fixed to the scalp or skull 32. Stereotactic equipment suitable to aid in placement of an electrical stimulation lead 14 in the brain may be positioned around the head. An insertion cannula for electrical stimulation lead 14 may be inserted through the burr hole into the brain at step 108, but a cannula is not typically used where lead 14 is a laminotomy or paddle style lead 14. A cannula and electrical stimulation lead 14 may be inserted together or lead 14 may be inserted through the cannula after the cannula has been inserted. Guided by the navigation system that includes the fMRI data obtained at step 100, electrical stimulation lead 14 is precisely positioned adjacent the brain at step 110 such that one or more electrodes 18 are located adjacent target brain tissue within the area of cortical reorganization 38 in the temporal lobe 34. In certain embodiments, electrical stimulation lead 14 is positioned extradurally, such as shown in FIG. 4.

At step 112, stimulation source 12 is activated, which generates and sends electrical signals via electrical stimulation lead 14 to the adjacent brain tissue. At step 114, the person indicates whether the tinnitus is suppressed by electrical stimulation system 10. If the tinnitus is not suppressed, electrical stimulation lead 14 may be moved incrementally at step 116 until the person indicates that the tinnitus is suppressed. Once electrical stimulation lead 14 has been properly positioned in the brain such that the tinnitus is suppressed, lead 14 is uncoupled from any stereotactic equipment present, and any cannula and the stereotactic equipment are removed at step 118. Where stereotactic equipment is used, any cannula may be removed before, during, or after removal of the stereotactic equipment. Connecting portion 16 of electrical stimulation lead 14 is laid substantially flat along the skull 32. Where appropriate, any burr hole cover seated in the burr hole may be used to secure electrical stimulation lead 14 in position and possibly to help prevent leakage from the burr hole and entry of contaminants into the burr hole. Example burr hole covers that may be appropriate in certain embodiments are illustrated and described in copending U.S. Provisional Application Nos. 60/528,604 and 60/528,689, both filed Dec. 11, 2003 and entitled "Electrical Stimulation System and Associated Apparatus for Securing an Electrical Stimulation Lead in Position in a Person's Brain".

Once electrical stimulation lead 14 has been inserted and secured, stimulation source 12 is implanted at step 120. The implant site is typically a subcutaneous pocket formed to receive and house stimulation source 12. The implant site is usually positioned a distance away from the insertion site, such as near the chest area or buttocks or another place in the torso 40. Connecting portion 16 of lead 14 extends from the lead insertion site to the implant site at which stimulation source 12 is implanted. Once all appropriate components of stimulation system 10 are implanted, these components may be subject to mechanical forces and movement in response to movement of the person's body. A doctor, the patient, or another user of stimulation source 12 may directly or indirectly input signal parameters for controlling the nature of the electrical stimulation provided.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 10 into a person for electrical stimulation of the person's brain.

During the operation of stimulation system 10 according to a particular set of stimulation parameters, the efficacy of the stimulation associated with the particular set of stimulation parameters may decrease over time due to neuroplasticity of the brain. Neuroplasticity refers to the ability of the brain to dynamically reorganize itself in response to certain stimuli to form new neural connections. This allows the neurons in the brain to compensate for injury or disease and adjust their activity in response to new situations or changes in their environment. With respect to electrical stimulation, the reduction in efficacy due to neuroplasticity can occur after just a few weeks of treatment. In order to regain the same efficacy, a new set of efficacious electrical stimulation parameters must be determined, the new set of parameters must be entered into the system, and the system is again used to electrically stimulate the brain according to the new set of parameters to continue to treat the condition. This may result in the additional time and expense associated with a return visit to the treating physician for determining and entering the new set of parameters. Especially where treatment is to continue over a relatively long period of time, such as months or years, this additional time and expense poses a significant drawback.

Thus, in certain embodiments, in addition to providing electrical stimulation to the temporal lobe 34 for tinnitus relief, stimulation system 10 may be capable of applying additional electrical stimulation to the temporal lobe 34 to reduce neuroplasticity effects associated with the therapeutic electrical stimulation. In one embodiment, the nature of the neuroplasticity reducing electrical stimulation may be varied more or less continually, in a predetermined or randomized manner, to prevent, delay, or otherwise reduce the ability of the brain to adapt to the neuroplasticity reducing electrical stimulation and dynamically reorganize itself accordingly. In a more particular embodiment, the neuroplasticity reducing electrical stimulation may be randomized or otherwise varied about the tinnitus reducing electrical stimulation to achieve this result. In essence, the randomized or otherwise varied neuroplasticity reducing electrical stimulation makes it more difficult for the brain to dynamically reorganize itself to overcome the effects of the tinnitus reducing electrical stimulation.

Figure 6:
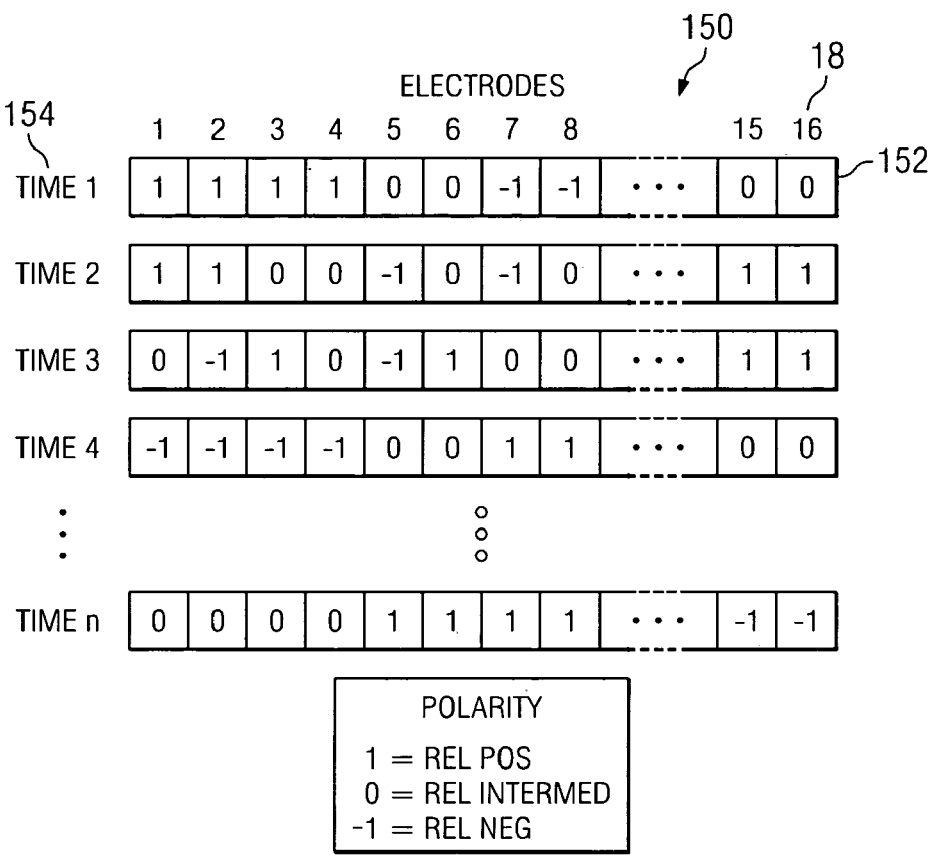
FIG. 6 illustrates an example stimulation set.

FIG. 6 illustrates an example stimulation set 150. One or more stimulation sets 150 may be provided, each stimulation set 150 specifying a number of stimulation parameters for the stimulation set 150. For example, as described more fully below with reference to FIGS. 7-8, multiple stimulation sets 150 may be executed in an appropriate sequence according to a pre-programmed or randomized stimulation program. Stimulation parameters for a stimulation set 150 may include an amplitude, a frequency, phase information, and a pulse width for each of a series of stimulation pulses that electrodes 18 are to deliver to the target brain tissue during a time interval during which stimulation set 150 is executed, along with a polarity 152 for each electrode 18 within each stimulation pulse. Stimulation parameters may also include a pulse shape, for example, biphasic cathode first, biphasic anode first, or any other suitable pulse shape.

For reducing neuroplasticity effects associated with therapeutic electrical stimulation, one or more stimulation parameters for a stimulation set 150 may be randomized or otherwise varied in any suitable manner within the time interval in which stimulation set 150 is executed, spanning one or more stimulation pulses within each stimulation pulse. For example, instead of or in addition to randomizing or otherwise varying polarities 152 for electrodes 18 as described below, the amplitude, frequency, phase information, and pulse width may be randomized or otherwise varied within predetermined ranges, singly or in any suitable combination, within each stimulation pulse. As another example, instead of or in addition to randomizing or otherwise varying polarities 152 for electrodes 18 over multiple stimulation pulses as described more fully below, the amplitude, frequency, phase information, and pulse width may be randomized or otherwise varied within predetermined ranges, singly or in any suitable combination, over multiple stimulation pulses, where the combination of stimulation parameters is substantially constant within each stimulation pulse but different for successive stimulation pulses. Such randomization or other variation of stimulation parameters for a stimulation set 150 reduces the ability of the brain to adapt to the neuroplasticity reducing electrical stimulation and dynamically reorganize itself to overcome the effects of the neuroplasticity reducing stimulation.

The polarity for an electrode 18 at a time 154 beginning a corresponding stimulation pulse or sub-interval within a stimulation pulse may be a relatively positive polarity 152, a relatively negative polarity 152, or an intermediate polarity 152 between the relatively positive polarity 152 and relatively negative polarity 152. For example, the relatively positive polarity 152 may involve a positive voltage, the relatively negative polarity 152 may involve a negative voltage, and the relatively intermediate polarity 152 may involve a zero voltage (i.e. "high impedance"). As another example, the relatively positive polarity 152 may involve a first negative voltage, the relatively negative polarity 152 may involve a second negative voltage more negative than the first negative voltage, and the relatively intermediate polarity 152 may involve a negative voltage between the first and second negative voltages. The availability of three distinct polarities 152 for an electrode 18 may be referred to as "tri-state" electrode operation. The polarity 152 for each electrode 18 may change for each of the sequence of times 154 corresponding to stimulation pulses or to sub-intervals within a stimulation pulse according to the stimulation parameters specified for the stimulation set 150. For example, as is illustrated in FIG. 6 for an example stimulation set 150 for a lead 14 with sixteen electrodes 18, the polarities 152 of the sixteen electrodes 18 may change for each of the sequence of times 154. In the example of FIG. 6, a relatively positive polarity 152 is represented using a "1," a relatively intermediate polarity 152 is represented using a "0," and a relatively negative polarity 152 is represented using a "−1," although any suitable values or other representations may be used.

Where appropriate, the polarity 152 for each electrode 18 may change in a predetermined or randomized manner, randomized changes possibly being more effective with respect to any neuroplasticity reducing stimulation for reasons described above.

Where stimulation system 10 provides, in addition to therapeutic electrical stimulation, electrical stimulation to reduce neuroplasticity effects associated with the therapeutic electrical stimulation, each stimulation pulse or sub-interval within a stimulation pulse may be particular to the stimulation being provided; that is, either to therapeutic electrical stimulation or to neuroplasticity reducing electrical stimulation. For example, one or more stimulation pulses or sub-intervals may be designed to provide therapeutic electrical stimulation and one or more other stimulation pulses or sub-intervals may be designed to reduce neuroplasticity effects. In this case, the therapeutic stimulation pulses or sub-intervals and neuroplasticity reducing stimulation pulses or sub-intervals may be arranged temporally in any suitable manner. A therapeutic stimulation pulse or sub-interval may be separated from a successive therapeutic stimulation pulse or sub-interval by any number of neuroplasticity reducing stimulation pulses or sub-intervals and this number may be the same between each pair of therapeutic stimulation pulses or sub-intervals or may vary between each pair of therapeutic stimulation pulses or sub-intervals in a predetermined or randomized manner. As another example, one or more stimulation pulses or sub-intervals may be designed to concurrently provide both therapeutic and neuroplasticity reducing electrical stimulation.

Similarly, where stimulation system 10 provides, in addition to therapeutic electrical stimulation, electrical stimulation to reduce neuroplasticity effects associated with the therapeutic electrical stimulation, each stimulation set 150 may be particular to either the therapeutic electrical stimulation or the neuroplasticity reducing electrical stimulation. For example, one or more stimulation sets 150 may be designed to provide therapeutic electrical stimulation and one or more other stimulation sets 150 may be designed to reduce neuroplasticity effects. In this case, the therapeutic stimulation sets 150 and neuroplasticity reducing stimulation sets 150 may be arranged temporally in any suitable manner. A therapeutic stimulation set 150 may be separated from a successive therapeutic stimulation set 150 by any number of neuroplasticity reducing stimulation sets 150 and this number may be the same between each pair of therapeutic stimulation sets 150 or may vary between each pair of therapeutic stimulation sets 150 in a predetermined or randomized manner. As another example, one or more stimulation sets 150 may be designed to concurrently provide both therapeutic and neuroplasticity reducing electrical stimulation.

In addition, the amplitude, frequency, phase information, or pulse width for a stimulation set 150 may be particular to the stimulation being provided. For example, therapeutic electrical stimulation may be provided using higher amplitude electrical energy than is used for neuroplasticity reducing electrical stimulation. In this case, the neuroplasticity reducing electrical stimulation may be below the therapeutic target threshold stimulation (i.e. below the threshold where therapeutic electrical stimulation is provided to treat a neurological or other disorder). Alternatively, neuroplasticity reducing electrical stimulation may be provided using the same or a higher amplitude electrical energy than is used for therapeutic electrical stimulation (i.e. at or above the threshold where therapeutic electrical stimulation is provided to treat the neurological or other disorder). In this case, the neuroplasticity reducing electrical stimulation's primary purpose is not to produce a therapeutic effect, but rather to reduce neuroplasticity. In this manner, the neuroplasticity reducing electrical stimulation could have both a therapeutic and neuroplasticity reducing effect.

Figure 8:
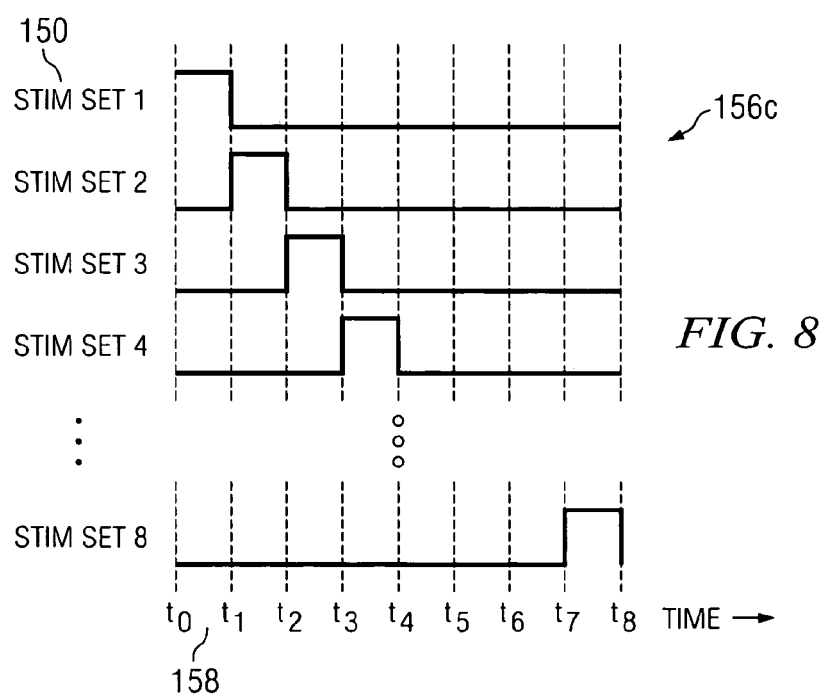
FIG. 8 illustrates example execution of a sequence of stimulation sets within an example stimulation program.
Figure 2A:
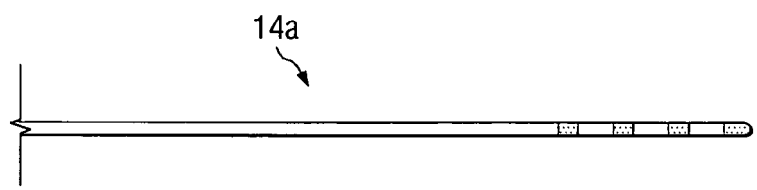
FIGS. 2A-2I illustrate example electrical stimulation leads that may be used to treat tinnitus and, in certain embodiments, provide reduced neuroplasticity effects in a person's brain.
Figure 2B:
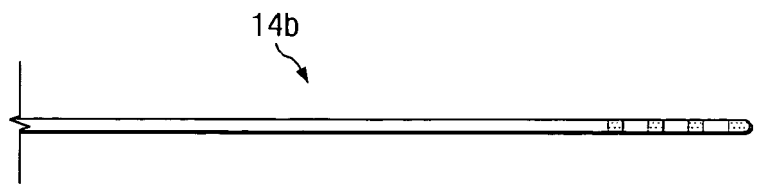
Figure 2C:
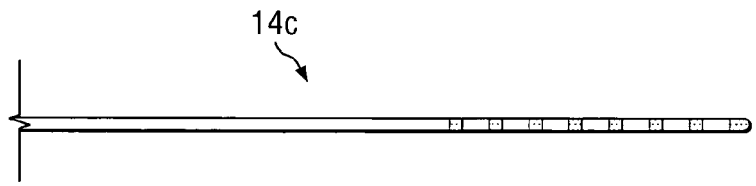
Figure 2D:
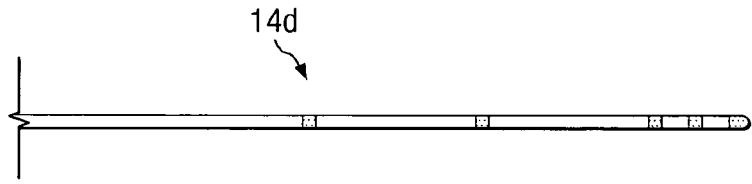
Figure 2E:
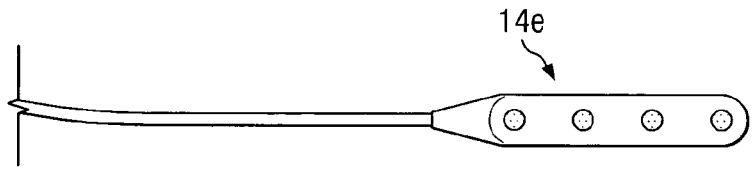
Figure 2F:
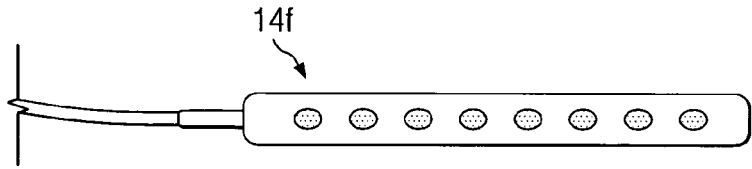
Figure 2G:
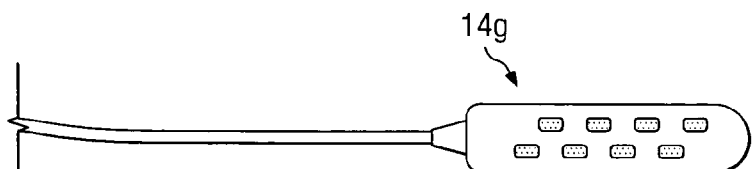
Figure 2H:
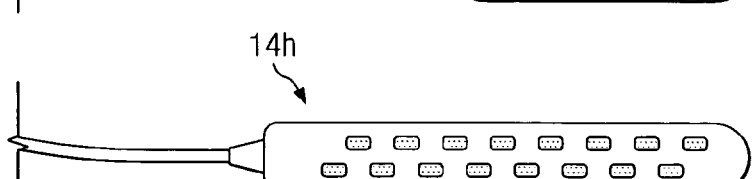
Figure 2I:
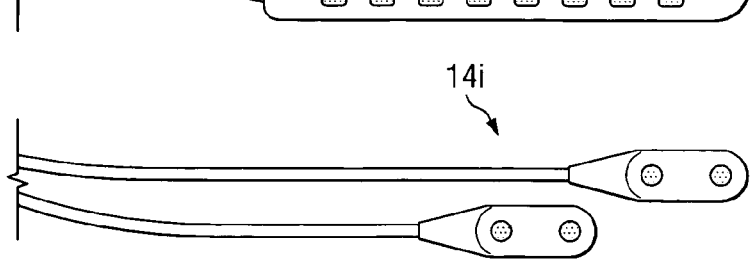
Figure 7:
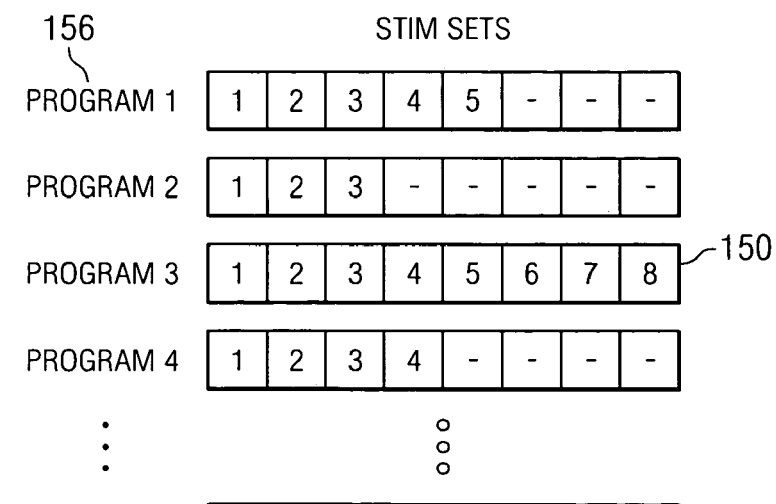
FIG. 7 illustrates a number of example stimulation programs, each of which includes a number of stimulation sets.

FIG. 7 illustrates a number of example stimulation programs 156, each including a number of stimulation sets 150. One or more simulation programs 156 may be set up to provide reduced neuroplasticity effects associated with therapeutic electrical stimulation of the brain. As described above, each stimulation set 150 specifies a number of stimulation parameters for the stimulation set 150. In one embodiment, within each stimulation program 156, stimulation system 10 consecutively executes the sequence of one or more stimulation sets 150 associated with stimulation program 156. The sequence may be executed only once, repeated a specified number of times, or repeated an unspecified number of times within a specified time period. For example, as is illustrated in FIG. 8 for the third example stimulation program 156c including eight stimulation sets 150, each of the eight stimulation sets 150 is consecutively executed in sequence. Although the time intervals 158 ($t_1$-$t_0$, $t_2$-$t_1$, etc.) during which the stimulation sets 150 are executed are shown as being equal, the present invention contemplates a particular stimulation set 150 being executed over a different time interval 158 than one or more other stimulation sets 150 according to particular needs. One or more stimulation sets 150 within at least one stimulation program 156 may be set up to provide reduced neuroplasticity effects associated with therapeutic electrical stimulation of the brain.

Although stimulation system 10 is illustrated by way of example as accommodating up to twenty-four stimulation programs 156 each including up to eight stimulation sets 150, the present invention contemplates any appropriate number of stimulation programs 156 each including any appropriate number of stimulation sets 150. For example, in a very simple case, a single stimulation program 156 may include a single stimulation set 150, whereas in a very complex case more than twenty-four stimulation programs 156 may each include more than eight stimulation sets 150.

In one embodiment, stimulation system 10 executes only a single stimulation program 156 in response to user selection of that stimulation program for execution. In another embodiment, during a stimulation period, stimulation system 10 executes a sequence of pre-programmed stimulation programs 156 for each lead 14 until the stimulation period ends. Depending on the length of the stimulation period and the time required to execute a sequence of stimulation programs 156, the sequence may be executed one or more times. For example, the stimulation period may be defined in terms of a predetermined number of cycles each involving a single execution of the sequence of stimulation programs 156, the sequence of stimulation programs 156 being executed until the predetermined number of cycles has been completed. As another example, the stimulation period may be defined in terms of time, the sequence of stimulation programs 156 being executed until a predetermined time interval has elapsed or the patient or another user manually ends the stimulation period. Although a sequence of stimulation programs 156 is described, the present invention contemplates a single stimulation program being executed one or more times during a stimulation period according to particular needs. Furthermore, the present invention contemplates each stimulation program 156 being executed substantially immediately after execution of a previous stimulation program 156 or being executed after a suitable time interval has elapsed since completion of the previous stimulation program 156. Where stimulation system 10 includes multiple leads 14, stimulation programs 156 for a particular lead 14 may be executed substantially simultaneously as stimulation programs 156 for one or more other leads 14, may be alternated with stimulation programs 156 for one or more other leads 14, or may be arranged in any other suitable manner with respect to stimulation programs 156 for one or more other leads 14.

Where stimulation system 10 provides, in addition to therapeutic electrical stimulation, electrical stimulation to reduce neuroplasticity effects, each stimulation program 156 may be particular to either the therapeutic electrical stimulation or the neuroplasticity reducing electrical stimulation. For example, one or more stimulation programs 156 may be designed to provide therapeutic electrical stimulation and one or more other stimulation programs 156 may be designed to reduce neuroplasticity effects. In this case, the therapeutic stimulation programs 156 and the neuroplasticity reducing stimulation programs 156 may be arranged temporally in any manner. A therapeutic stimulation program 156 may be separated from a successive therapeutic stimulation program 156 by any number of neuroplasticity reducing stimulation programs 156 and this number may be the same between each pair of therapeutic stimulation programs 156 or may vary between each pair of therapeutic stimulation programs 156 in a predetermined or randomized manner. As another example, one or more stimulation programs 156 may be set up to concurrently provide both therapeutic and neuroplasticity reducing electrical stimulation.

In general, each stimulation program 156 may, but need not necessarily, be set up for electrical stimulation of different target brain tissue. As an example, where therapeutic electrical stimulation of the temporal lobe 34 is desired, one or more stimulation programs 156 may be set up for therapeutic electrical stimulation of target brain tissue in the temporal lobe 34 and one or more other stimulation programs 156 may be set up for electrical stimulation of the same target brain tissue in the temporal lobe 34 to reduce neuroplasticity effects associated with the therapeutic electrical stimulation. As another example, where therapeutic electrical stimulation of the auditory cortex 34 is desired, one or more stimulation programs 156 may be set up for therapeutic electrical stimulation of target brain tissue in the temporal lobe 34 and one or more other stimulation programs 156 may be set up for electrical stimulation of different target brain tissue in the temporal lobe 34 or elsewhere in the brain to reduce neuroplasticity effects associated with the therapeutic electrical stimulation.

As described above, in one embodiment, the nature of any neuroplasticity reducing electrical stimulation may be varied more or less continually, whether in a predetermined or randomized manner, to prevent, delay, or otherwise reduce the ability of the brain to adapt to the neuroplasticity reducing electrical stimulation and dynamically reorganize itself accordingly. In a more particular embodiment, where the neuroplasticity reducing electrical stimulation is provided concurrently with therapeutic electrical stimulation, the neuroplasticity reducing electrical stimulation may be randomized or otherwise varied about the therapeutic electrical stimulation to achieve this result. In essence, the randomized or otherwise varied neuroplasticity reducing electrical stimulation makes it more difficult for the brain to dynamically reorganize itself to overcome the effects of the therapeutic electrical stimulation.

The present invention contemplates any suitable circuitry within stimulation source 12 for generating and transmitting signals for electrical stimulation of a person's brain to treat tinnitus and, where appropriate, provide reduced neuroplasticity effects, whether separate from or concurrently with the therapeutic electrical stimulation. Example circuitry which may be used is illustrated and described in U.S. Pat. No. 6,609,031 B1, which is hereby incorporated by reference herein as if fully illustrated and described herein.

Although the present invention has been described above in connection with several embodiments, a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A method for reducing tinnitus, comprising:
   identifying tinnitus in a person;
   using a stimulation source to generate electrical stimulation energy; and
   using electrodes of an electrical stimulation lead, the electrodes being implanted extradurally on the person's cortex proximate to target brain tissue, to deliver electrical stimulation energy from the stimulation source to the target brain tissue located in the person's temporal lobe to reduce tinnitus effects, wherein the target brain tissue is located in an area of cortical reorganization.

2. The method of claim 1, wherein the electrical stimulation lead is implanted into an extradural region adjacent the brain such that one or more of the electrodes are located immediately against the person's dura.

3. The method of claim 1, wherein the target brain tissue is located in an area of the brain selected from the group consisting of:
   the secondary auditory cortex;
   Brodmann area 22; and
   Brodmann area 52.

4. The method of claim 1, wherein the electrical stimulation lead is a laminotomy or paddle style lead.

5. The method of claim 1, further comprising:
   implanting the electrical stimulation lead into an extradural region adjacent the brain such that one or more of the electrodes are located adjacent the temporal lobe;
   receiving feedback from the person regarding the level of suppression of the tinnitus effects experienced by the person;
   moving the electrical stimulation lead based on the received feedback until a desired level of suppression of the tinnitus effects is achieved; and
   securing the electrical stimulation lead in the position in which the desired level of suppression of the tinnitus effects is achieved.

6. The method of claim 1, further comprising:
   performing an auditory functional imaging of the person's brain to generate images of the brain and to locate an area of cortical reorganization in the temporal lobe;
   loading the results of the auditory functional imaging into a neuronavigation system;
   implanting the electrical stimulation lead onto an extradural region adjacent the brain; and
   using the neuronavigation system to guide the electrical stimulation lead such that one or more of the electrodes are located adjacent the area of cortical reorganization.

7. The method of claim 1, further comprising:
   performing transcranial magnetic stimulation of an area of cortical reorganization in the temporal lobe of the person's brain to determine whether the person is a candidate for receiving an implanted electrical stimulation lead;
   if it is determined based on the transcranial magnetic stimulation that the person is a candidate for receiving an implanted electrical stimulation lead, implanting the electrical stimulation lead into an extradural region adjacent the brain such that one or more of the electrodes are located adjacent the area of cortical reorganization within the temporal lobe.

8. The method of claim 7, further comprising:
performing an auditory functional imaging of the person's brain to generate images of the brain and to locate the area of cortical reorganization in the temporal lobe;
loading the results of the auditory functional imaging into a neuronavigation system;
performing the transcranial magnetic stimulation using the neuronavigation system; and
using the neuronavigation system to guide the implanted electrical stimulation lead such that one or more of the electrodes are located adjacent the area of cortical reorganization.

9. The method of claim 7, further comprising using the stimulation source to generate signals for transmission to the electrodes to cause the electrodes to deliver electrical stimulation energy to the target brain tissue to provide neuroplasticity reducing electrical stimulation of the target brain tissue in addition to tinnitus reducing electrical stimulation, the neuroplasticity reducing electrical stimulation making it more difficult for the brain to dynamically reorganize itself to overcome effects of the tinnitus reducing electrical stimulation.

10. The method of claim 9, wherein the neuroplasticity reducing electrical stimulation is randomized to make it more difficult for the brain to adapt to the neuroplasticity reducing electrical stimulation and dynamically reorganize itself accordingly.

11. The method of claim 9, wherein the stimulation source is operable to generate the signals for reducing tinnitus effects in association with the signals generated for reducing neuroplasticity effects, such that the electrodes are caused to deliver electrical energy for reducing tinnitus effects and electrical energy for reducing neuroplasticity effects substantially concurrently to the target brain tissue.

12. The method of claim 9, wherein the neuroplasticity reducing electrical stimulation is randomized about the electrical stimulation for reducing tinnitus effects.

13. The method of claim 9, wherein the average intensity of the electrical stimulation energy delivered to reduce neuroplasticity effects is less than or equal to average intensity of the electrical stimulation energy delivered to reduce tinnitus effects.

14. The method of claim 9, wherein the stimulation source generates the signals according to one or more stimulation sets each specifying a plurality of stimulation parameters, the stimulation parameters for a stimulation set comprising a polarity for each electrode at each of one or more times within a stimulation pulse for the stimulation set.

15. The method of claim 9, wherein the stimulation source generates the signals according to one or more stimulation sets each specifying a plurality of stimulation parameters for a plurality of stimulation pulses, one or more of the stimulation pulses accomplishing tinnitus reducing electrical stimulation of the target brain tissue and one or more other of the stimulation pulses accomplishing neuroplasticity reducing electrical stimulation of the target brain tissue.

16. The method of claim 9, wherein the stimulation source generates the signals according to a plurality of stimulation programs each comprising one or more stimulation sets, each stimulation set specifying a plurality of stimulation parameters, one or more of the stimulation sets accomplishing tinnitus reducing electrical stimulation of the target brain tissue and one or more other of the stimulation sets accomplishing neuroplasticity reducing electrical stimulation of the target brain tissue.

17. A method for treating tinnitus, comprising:
identifying tinnitus in a person;
placing an electrical stimulation lead extradurally on the person's cortex, wherein the lead is positioned adjacent to target brain tissue in the person's temporal lobe, wherein the target brain tissue is located in an area of cortical reorganization; and
using the electrical stimulation lead to stimulate the target brain tissue in the person's temporal lobe, the stimulation reducing tinnitus effects.

18. The method of claim 17, wherein the target brain tissue is located in an area of the brain selected from the group consisting of:
the secondary auditory cortex;
Brodmann area 22; and
Brodmann area 52.

19. A method of treating tinnitus in a patient, comprising:
identifying tinnitus in a patient;
generating electrical pulses using an implantable pulse generator (IPG) that is implanted within the patient;
conducting the electrical pulses from the IPG through a stimulation lead; and
applying the electrical pulses to stimulate neural tissue of the patient utilizing one or several electrodes of the stimulation lead, wherein electrodes of the stimulation lead are positioned substantially adjacent to the cortex of the patient and wherein all electrodes of the stimulation lead are positioned extradurally, wherein the applying the electrical pulses effectively treats tinnitus of the patient;
wherein the generating, conducting, and applying are performed on a chronic basis.

20. The method of claim 19 wherein neural tissue stimulated by the electrical pulses comprises an area of cortical reorganization in an area of the brain selected from the group consisting of:
the secondary auditory cortex;
Brodmann area 22; and
Brodmann area 52.

21. The method of claim 19 wherein the stimulation lead is a laminotomy or paddle style lead.

22. The method of claim 19 further comprising:
implanting the stimulation lead into an extradural region adjacent the cortex such that one or more of the electrodes are located adjacent to the cortex;
receiving feedback from the patient regarding the level of suppression of the tinnitus effects experienced by the patient;
moving the stimulation lead based on the received feedback until a desired level of suppression of the tinnitus effects is achieved; and
securing the electrical stimulation lead in the position in which the desired level of suppression of the tinnitus effects is achieved.

23. The method of claim 19, further comprising:
performing an auditory functional imaging of the patient's brain to generate images of the brain and to locate the area of cortical reorganization;
loading the results of the auditory functional imaging into a neuronavigation system;
implanting the stimulation lead into an extradural region adjacent the brain; and
using the neuronavigation system to guide the stimulation lead such that one or more of the electrodes are located adjacent the area of cortical reorganization.

* * * * *